United States Patent [19]

Hocks et al.

[11] 4,222,393
[45] Sep. 16, 1980

[54] TINNITUS MASKER

[75] Inventors: Robert W. Hocks; Jack A. Vernon, both of Portland, Oreg.

[73] Assignee: American Tinnitus Association, Portland, Oreg.

[21] Appl. No.: 929,032

[22] Filed: Jul. 28, 1978

[51] Int. Cl.³ .................. A61B 5/00; A61B 5/12; A61M 21/00
[52] U.S. Cl. .................. 128/746; 128/1 C; 179/107 FD
[58] Field of Search ............ 128/1 R, 905, 1 C, 746; 179/107 FD

[56] References Cited

U.S. PATENT DOCUMENTS

| | | | |
|---|---|---|---|
| 2,235,733 | 3/1941 | Witting | 128/746 |
| 3,349,179 | 10/1967 | Klein | 179/1 |
| 3,394,698 | 7/1968 | Calkins | 128/1 C |
| 3,884,218 | 5/1975 | Monroe | 128/1 C |
| 3,993,043 | 11/1976 | Adams et al. | 128/1 C |
| 4,034,741 | 7/1977 | Adams et al. | 128/1 C |
| 4,047,377 | 9/1977 | Banks, Jr. | 128/1 C |

OTHER PUBLICATIONS

P. 1307, "Sears Fall and Winter Catalog, 1969", Item (1), Sick Bed Accessories.
P. 476, "Sears Wish Book for the 1979 Holiday Season", Item (4), Sleepmate.

*Primary Examiner*—Willis Little
*Attorney, Agent, or Firm*—Lee R. Schermerhorn

[57] ABSTRACT

A tinnitus patient is subjected to external sounds of different pitch, one after another, to enable the patient to identify the particular external sound having the same pitch as the subjective tinnitus sound perceived by the patient. Then the patient is provided with a power operated sound generator producing a range of frequencies extending above and below said perceived pitch to mask the tinnitus sound. The sound generator may be worn in the same manner as a hearing aid and may be combined with a hearing aid if necessary.

4 Claims, 8 Drawing Figures

TINNITUS MASKER

BACKGROUND OF THE INVENTION

This invention relates to improvements in the masking of subjective sounds perceived by tinnitus sufferers.

Tinnitus is defined as any ringing in the ears for which there is no external source. It can be merely annoying or it can be of excruciating distress and severity. It can be intermittent and it can be continuous. Prior to the present invention there has been no effective relief. Previous attempts to mask the subjective sound perceived by the sufferer have not been successful.

One of the reasons for the previous lack of success in attempting relief is the elusive character of the malady. In attempting to determine the pitch of the offending subjective sound it is often found that the sufferer is in error in the magnitude of one octave. Extremely confusing in many cases is the intermittent nature of the subjective sound. Often, when successful masking is thought to be achieved, it is found that the subjective sound has merely ceased for a time of its own accord, only to return in its original intensity at some later time.

Another difficulty in affording relief is that the pitch of the offending subjective sound may change from time to time. An external masker sound of a given frequency may be effective at one time and not at some other time. Persistent and repeated testing of the patient are necessary.

Objects of the present invention are therefore to provide an improved method and apparatus for the masking of tinnitus, to provide a tinnitus masker which is capable of coping with the variable characteristics of the malady and to provide an effective power operated masker which may conveniently be worn in the same manner as a hearing aid or which may be combined with a hearing aid.

SUMMARY OF THE INVENTION

According to the present invention a tinnitus sufferer is first tested to determine the pitch of the offending subjective sound. This is down by subjecting the patient to sounds of different pitch in small increments over a wide range. When the patient indentifies a sound of a particular pitch that seems to correspond to the pitch of the tinnitus noise the testing is continued with other sounds at various pitches removed to eliminate a possibility of identification errors in the patient's perception.

Such tests may have to be repeated many times. If the tinnitus ceases during such testing, the test sounds themselves may have been responsible for the relief, or the tinnitus sound may have stopped of its own accord because of its intermittent nature. In either case the testing cannot be resumed until the tinnitus sounds return. Repeated testing is also necessary to discover if there is a change of pitch of the tinnitus sound from time to time.

The results of such repeated testing may indicate a range of frequencies which must be supplied by the masker in order to be effective for the particular patient. The noise generated by the tinnitus masker is a narrow band of noise which is selected so as to include the frequency corresponding to the patient's tinnitus. Various bands of noise are made available so that the one which is appropriate for the given patient is available.

The power supply and sound generator may be applied to the patient as desired, on the body, in eye glasses, behind the ear, or within the ear. The masker may thus be worn in the same manner as a hearing aid and may be combined with a hearing aid. While such masking sound may not cure the tinnitus it does often afford a very pronounced relief from the discomfort of the tinnitus.

The invention will be better understood and additional objects and advantages will become apparent from the following detailed description of the preferred embodiments illustrated in the accompanying drawings. Various changes may be made in the details of the method and apparatus and certain features may be used without others. All such modifications within the scope of the appended claims are included in the invention.

DESCRIPTION OF THE PREFERRED EMBODIMENTS

Figure 1:
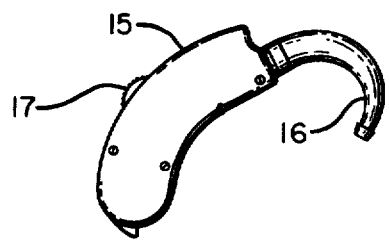
FIG. 1 is a side elevation view of a masker embodying the invention.

In FIG. 1 the masker housing 15 is adapted to be worn behind the ear in the manner of a hearing aid. A curved plastic tube 16 conveys the sound produced by a sound generator in housing 15 into the ear of the wearer. Housing 15 also contains a battery to supply power for the sound generator and a volumne control button 17.

Figure 2:
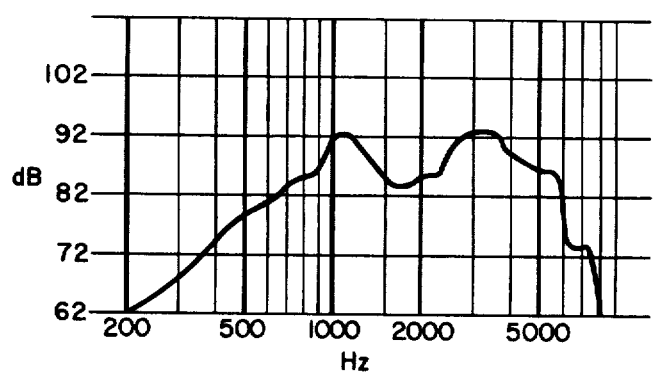
FIG. 2 is a masker output curve obtained from a wide band sound generator.

For some patients a wide band sound generator is prescribed, producing a sound output curve as illustrated in FIG. 2. The primary energy is produced between 1000 Hz and 5000 Hz.

Figure 3:
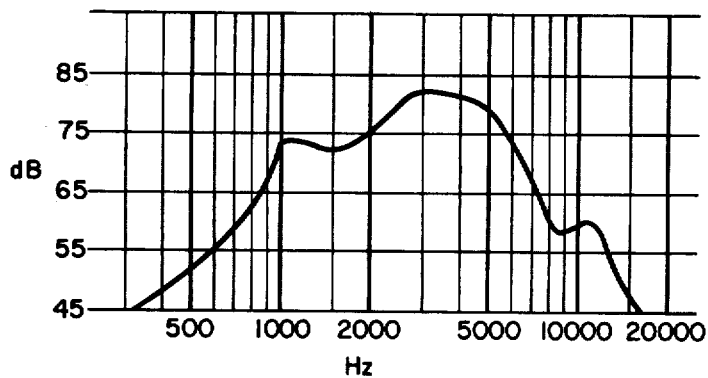
FIG. 3 is a masker output curve obtained from a sound generator with high frequency emphasis.

Some patients are better served with a sound generator having high frequency emphasis as illustrated by the output curve in FIG. 3. This curve extends from about 1000 Hz to 5000 Hz with a peak around 3000 or 4000 Hz and shows considerable energy at 10,000 Hz.

Figure 4:
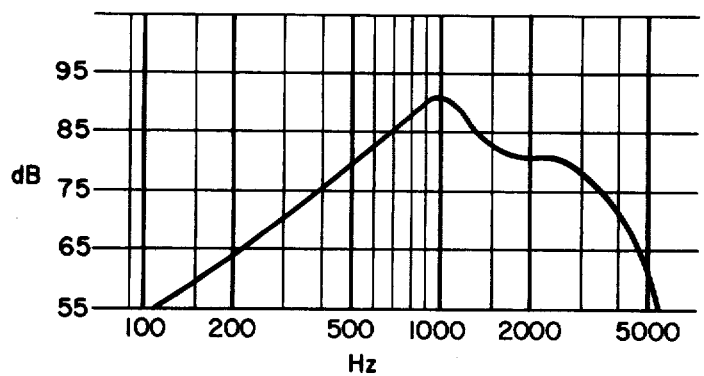
FIG. 4 is a masker output curve obtained from a sound generator having low frequency emphasis.

Other patients are best served by a sound generator having low frequency emphasis as illustrated in FIG. 4. This output curve increases to a maximum output at 1000 Hz and declines above that frequency.

The foregoing output measurements were made using a 2 cc acoustic coupler which comprises a closed cavity or chamber receiving sound output from tube 11, the output being measured in such chamber. The sound output may also be measured in a closed chamber which is a scientific reproduction of the human ear with all its acoustical reflections including the outer ear, the ear canal and the ear drum. Measurements made with such a device will vary to some extent from the results illustrated in FIGS. 2, 3 and 4 but the latter are adequate for the present purpose.

In each instance the sound generator produces all frequencies represented by the curve, which is referred to as a masking sound or masking noise. This is to be distinguished from sound generators which merely produce a single frequency or a small number of discreet frequencies, or white noise generators.

Figure 5:
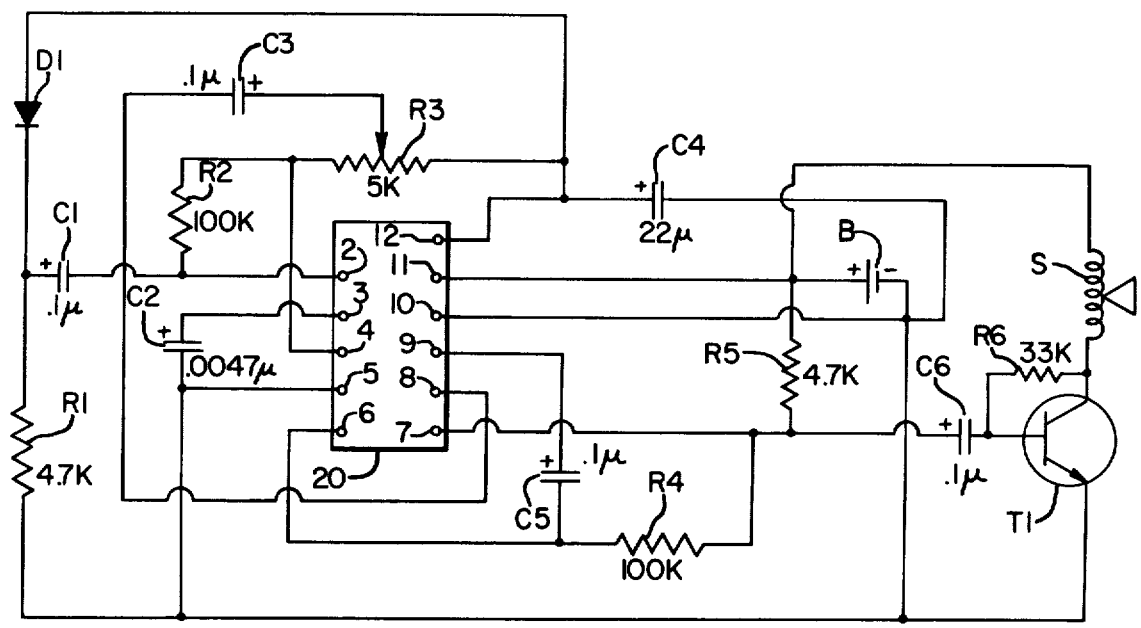
FIG. 5 is a wiring diagram for a broad band sound generator.

A circuit for producing a wide band sound output as illustrated in FIG. 2 is shown in FIG. 5. The block diagram 20 in FIG. 5 represents an intergrated circuit unit which is illustrated in detail in FIG. 6. FIG. 5 will accordingly be described with reference to FIG. 6. Integrated circuit unit 20 has eleven external pin connectors 2–12 as identified in FIGS. 5 and 6.

Figure 6:
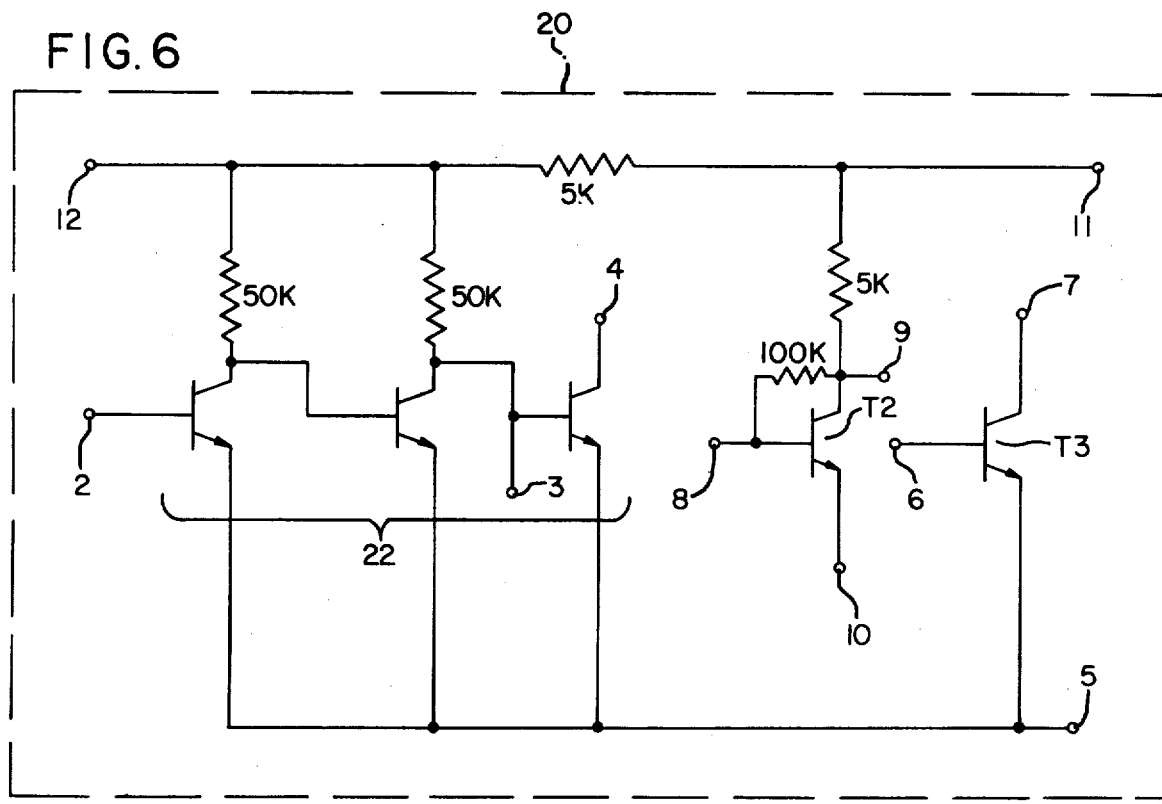
FIG. 6 is a wiring diagram for an intergrated circuit component contained within the system in FIG. 5.

The system, in FIGS. 5 and 6 contains one integrated circuit 20 and one output transistor T1 for the sound emitter S which may be referred to as a receiver. The integrated circuit 20 contains a three stage dc coupled amplifier 22 and two independent NPN transistors T2 and T3. The combination of pin 12 of integrated circuit 20 and capacitor C4 in FIG. 5 forms a voltage setting network, producing a 0.7 volt level supplied from battery B. This voltage provides the proper operation of the circuit. Resistor R1 serves a voltage divider for diode D1.

Pin 2 is capacitively coupled to the signal produced as described above through capacitance C1. Resistor R2 and resistor R3 form a voltage divider for the signal present on the minus side of capacitor C1. This signal is introduced to pin 8 of integrated circuit 20 via the voltage divider which is capacitively coupled to pin 8 thru capacitor C3. Pins 3 and 5 have a 0.0047 mfd capacitance C2 across them. This forms a high frequency limiting compensation network.

Resistor R4 forms a feedback loop from pin 7, which carries the output from the integrated circuit 20, to pin 6. Capacitor C5 which couples the signal out from pin 9 to pin 6 is the input of the final stage of integrated circuit 20. Resistor R5 serves as load supplying plus voltage to pin 7 of integrated circuit 20.

Transistor T1 is the output transistor for the masker sound emitter S. Resistor R6 provides self bias for transistor T1 and the transistors base is capacitively coupled to the output of integrated circuit 20 via capacitor C6. Resistor R3 is a potentiometer which also is the volume control 17 in FIG. 1, which can be varied up and down for the user's comfort and need.

Masker housing 15 in FIG. 1 contains a battery holder which pivots out of housing 15 for replacement of the battery and to disconnect the battery when the masker is not in use.

Figure 7:
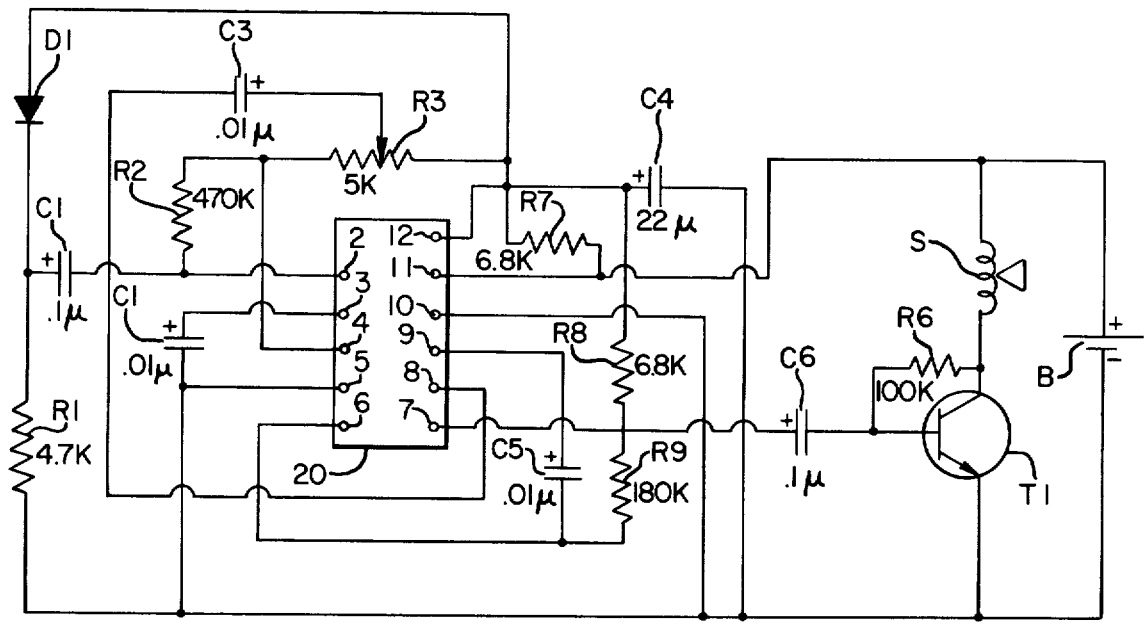
FIG. 7 is a wiring diagram for a sound generator having high frequency emphasis.

FIG. 7 illustrates a suitable circuit for a masker with high frequency emphasis as illustrated in FIG. 3. This is essentially the same as FIG. 5 except for added biasing and frequency emphasis networks. A more limited supply is used for frequency determination by adding resistor R7 to the circuit. The further addition of resistor R8 and resistor R9 provides more stable biasing. Together they form a voltage divider for pin 7 of integrated circuit 20. Resistor R6 in FIG. 5 is replaced with a 100 K resistor R6a to provide proper bias for transistor T1. Also the receiver S is changed to accomodate the emphasis for the higher frequencies involved.

Figure 8:
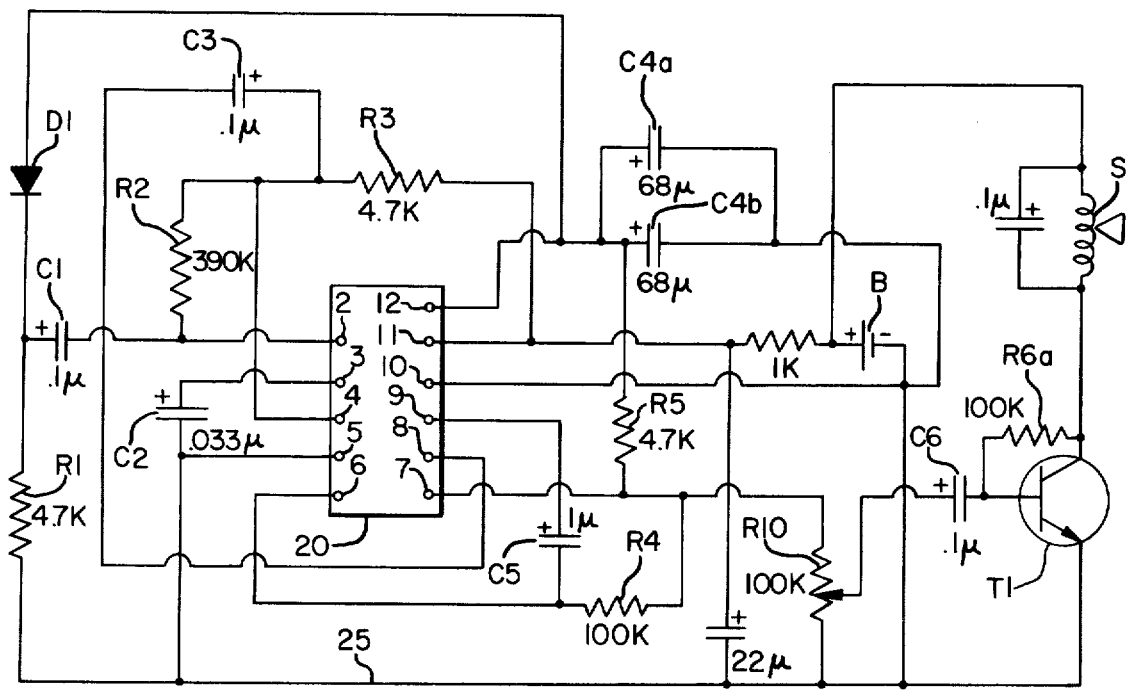
FIG. 8 is a wiring diagram for a sound generator having low frequency emphasis.

FIG. 8 illustrates a suitable circuit for a masker having low frequency emphasis as illustrated in FIG. 4. This circuit also varies only slightly from FIG. 5. The variation essentially concerns the introduction of a better filtered supply for the white noise generated by diode D1, involving two 68 mfd capacitors C4a and C4b, and a change in volume control location. This change in location involves also a new value of 100 K for potentiometer resistance R10. The output of integrated circuit 20 from pin 7 is presented to one leg of the potentiometer resistance R10 while the other leg is at circuit ground in wire 25. The movable contact of the potentiometer is coupled through capacitor C6 to transistor T1 and, as the potentiometer is varied, the transistor receives varying amounts of signal, thus making output amplitude go up or down.

What is claimed is:

1. The method of masking a tinnitus sensation of noise in a patient comprising subjecting the patient to external sounds of different pitch, one after another, to enable the patient to identify the particular external sound having the same pitch as the subjective tinnitus sensation of sound perceived by the patient, and then applying to the ear of the patient a power operated sound generator producing a noise output at all frequencies within a range of frequencies extending above and below said perceived pitch.

2. The method of claim 1 wherein the primary energy of said sound generator is produced between the frequencies of 1000 Hz and 5000 Hz.

3. The method of claim 2 wherein an effective amount of energy is produced at 10,000 Hz.

4. The method of claim 1 wherein the energy output of said sound generator increases to a maximum at 1000 Hz and then declines above that frequency.

* * * * *